United States Patent [19]

Wolthausen

[11] Patent Number: 4,548,081
[45] Date of Patent: Oct. 22, 1985

[54] ULTRASONIC SOFTNESS TESTING SYSTEM

[75] Inventor: Edward C. Wolthausen, Vancouver, Wash.

[73] Assignee: Crown Zellerbach Corporation, San Francisco, Calif.

[21] Appl. No.: 632,924

[22] Filed: Jul. 20, 1984

[51] Int. Cl.[4] ............................................. G01N 29/00
[52] U.S. Cl. .......................................... 73/584; 73/78; 73/159; 73/599; 73/627; 162/198; 162/263
[58] Field of Search ........................ 73/159, 78, 9, 584, 73/599, 627; 162/198, 263

[56] References Cited
U.S. PATENT DOCUMENTS

| | | | |
|---|---|---|---|
| 2,786,352 | 3/1957 | Sobota | 73/159 |
| 2,922,303 | 1/1960 | Veneklosen et al. | 73/159 |
| 3,151,483 | 10/1964 | Plummer | 73/159 |
| 3,683,681 | 8/1972 | Taylor | 73/159 |

*Primary Examiner*—Howard A. Birmiel
*Attorney, Agent, or Firm*—Thomas R. Lampe

[57] ABSTRACT

The softness of paper as a function of the number of bonding sites per unit area of the paper is determined by directing ultrasonic energy toward the paper and determining the magnitude of the portion of reflected energy.

22 Claims, 5 Drawing Figures

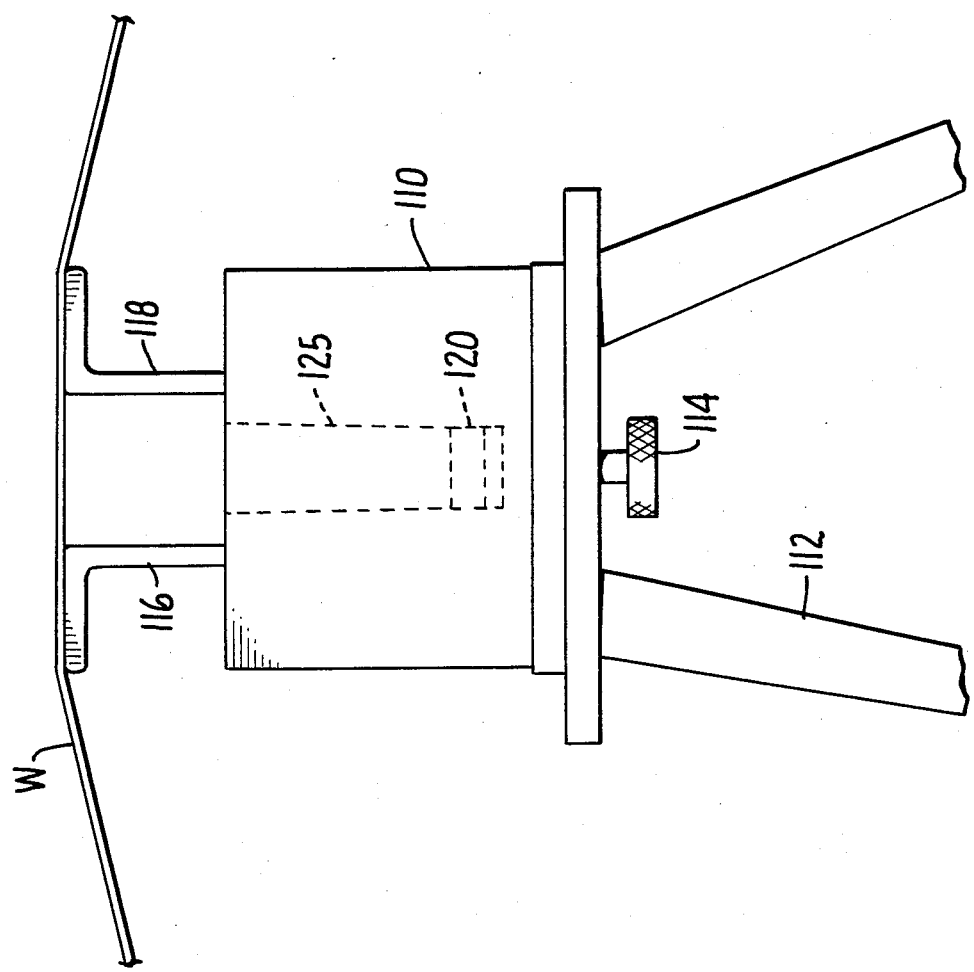
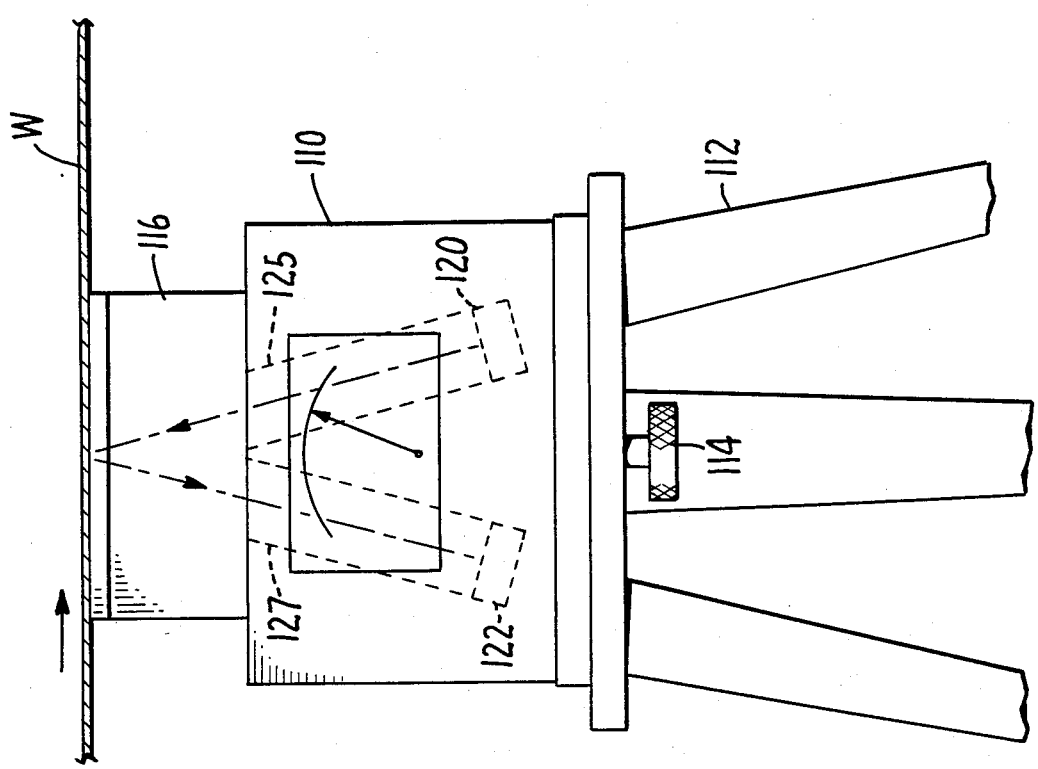

ULTRASONIC SOFTNESS TESTING SYSTEM

BACKGROUND OF INVENTION

The present invention relates to a system for testing the softness of paper.

A number of techniques have been employed in the past for testing the softness of paper and similar materials.

One such technique is disclosed in U.S. Pat. No. 3,683,681 issued Aug. 15, 1972 to R. E. Taylor. In that patent, paper is bent around a plurality of rods. This in turn causes the fibers in the paper to rub against each other and produce an ultrasonic signal. The level of this fiber generated signal is stated to be proportional to the roughness and other factors relating to the softness of the fibers. Specifically, a softer paper is alleged to produce a lower output signal level than will a harder paper. This signal is received by a microphone, amplified, and converted to an audible frequency signal.

U.S. Pat. No. 2,922,303 issued Jan. 26, 1980 to P. S. Veneklasen et al discloses a testing instrument wherein the hand of a textile, or the various properties which may affect the hand, are tested by rubbing a fixed sample of the fabric with a movable sample fabric. According to the patent, the vibration of fibrous elements during frictional engagement between the textile samples is converted to sound by impressing the vibrations through a diaphragm on a cavity. The variations in pressure (or sound) within the cavity are converted by a microphone into an electrical signal.

BRIEF SUMMARAY OF THE INVENTION

The apparatus and method of the present invention also employ a sonic technique to measure the softness of paper. However, the present approach allows testing to be conducted with a degree of accuracy not possible with prior art acoustic schemes.

Such accuracy is achieved by employing an ultrasonic signal to measure the number of bonding sites per unit area of the paper being tested. It has been found that, other factors being equal, an inverse relationship exists between the softness of a paper sheet and the number of its bonding sites per unit area.

According to the teachings of the present invention, ultrasonic energy is generated and transmitted to the surface of a sheet of paper. A portion of the transmitted ultrasonic energy is reflected from the paper as a function of the number of bonding sites per unit area of the paper. The magnitude of the reflected ultrasonic energy portion is then sensed.

BRIEF DESCRIPTION OF THE DRAWINGS

FIG. 4 is a frontal elevational view of an alternative embodiment of the invention; and FIG. 5 is a side view of the embodiment of FIG. 4.

DETAILED DESCRIPTION

Figure 1:
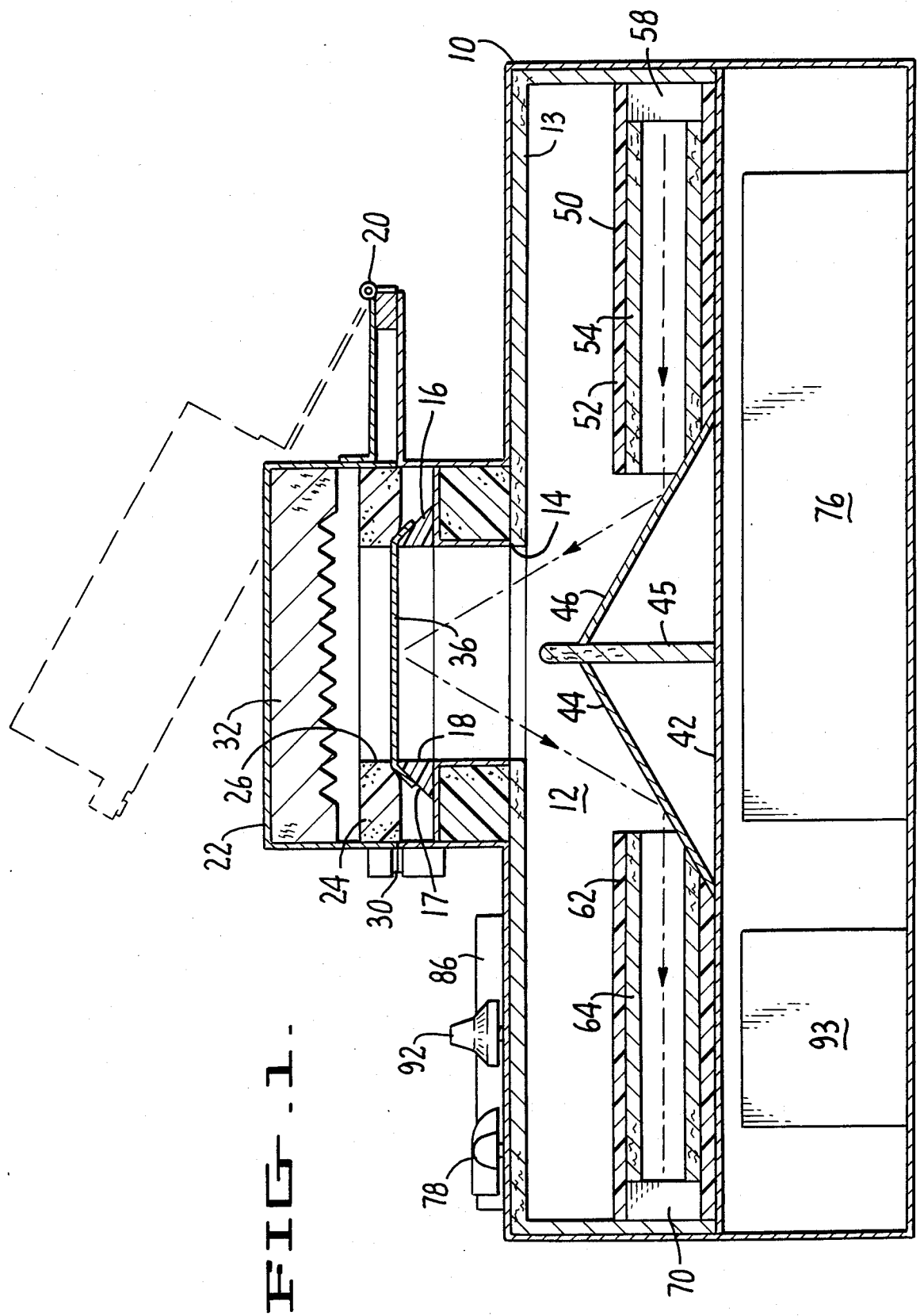
FIG. 1 is an elevational view partly in section of a preferred form of apparatus constructed in accordance with the teachings of the present invention.

Referring now to FIG. 1, a preferred form of apparatus constructed in accordance with the present invention includes a housing defining an interior 12 having sound insulating material such as felt liner 13 disposed thereabout. An aperture 14 is defined by the top wall of the housing, and disposed about the periphery of the aperture 14 on the top wall is a ring member 16. Ring member 16 has a sloped peripheral wall 17 and is preferably constructed of a material having a low coefficient of friction, such as tetraflouroethylene or high density polyethylene. Ring member 16 has an opening 18 generally corresponding to the size of aperture 14 and in registry therewith.

Hingedly attached to the remainder of the apparatus by means of a hinge member 20 is a closure element 22. Closure element 22 accomodates therein a sheet 24 constructed of low density foam rubber or other suitable sound insulating and absorbing material. Sheet 24 conforms in size to the interior of closure element 22 and has an aperture 26 formed therein which is adapted to register with opening 18 when the closure element 22 is closed as shown in solid lines in FIG. 1. A magnetic latch 30 is preferably employed to maintain the closure element 22 in closed position until the closure element is manually manipulated for opening to the position shown by the dash lines.

Positioned above sheet 24 and spaced therefrom is a second sheet 32 of sound insulating and absorbing material such as medium density, open cell foam rubber. The bottom of second sheet 32 preferably has projections formed on the lower surface thereof to enhance the sound absorbing and nonreflecting characteristics of second sheet 32.

Ring member 16 defines with sheet 24 upon closure of closure element 22 a sampling station for accomodating a sample or specimen 36 of the paper to be tested. When the closure element is latched in its closed position, sheet 24 and ring member 16 cooperate to clamp the outer periphery of the paper sample and insure that an area of the sample corresponding in size to opening 18 is exposed to interior 12. Movement of sheet 24 into clamping position causes the border of the sample to slide on wall 17 and tighten the sample over opening 18.

Interior 12 of the apparatus accomodates a base plate 42 from which project a pair of reflector plates 44 and 46 forming a generally triangular configuration with the base plate. The plates converge at a centrally positioned upstanding piece of felt or other sound insulating material 45. Reflector plates 44 and 46 have outwardly disposed reflection surfaces and may be formed of any suitable hard smooth sound reflecting material. Polished aluminum has been found to be one such acceptable material. The included angles between one reflector surface and the base and the other reflector surface and the base are substantially equal, and in the illustrated preferred embodiment such included angles are each in the order of 30°. The bottoms of the plates should be insulated from base plate 42 to ensure than an acoustical path is not established therealong.

Positioned immediately adjacent reflector plate 46 and to the right thereof as viewed in FIG. 1 is a conduit 50. Conduit 50 includes a rigid tubular outer portion 52 constructed of plastic, metal or the like defining an interior having a circular cross section and sound insulating liner material 54, such as felt, disposed about said interior. The end of the conduit most remote from reflector plate 46 accomodates therein an ultrasonic energy signal transducer 58, said transducer preferably being in the form of a piezoelectric crystal.

It will be appreciated that ultrasonic sound energy produced by transducer 58 will pass through conduit 50 and emerge therefrom in the form of a collimated beam of ultrasonic energy. The liner material 54 assists in the formation of the collimated beam. The beam, upon emergence from conduit 50, will reflect from reflector plate 46 and be directed as shown by the arrows in FIG. 1 to the surface of paper specimen 36.

A portion of the transmitted ultrasonic energy is reflected from paper specimen 36 as a function of the number of bonding sites per unit area of the paper. That is, the higher the number of bonding sites per unit area of paper, the larger the portion of the reflected energy. The energy not reflected will either pass through or be absorbed by the paper specimen. Any such energy passing through the specimen will be absorbed by sheet 32 and dissipate within the interior of the closure element 22.

The reflected portion of the ultrasonic energy will follow a path indicated by the arrows in FIG. 1 to a location on reflector plate 44. From that location the portion is reflected into a conduit 62 which is positioned in alignment with conduit 50. Conduit 62 is preferably constructed of the same materials as conduit 50 and includes a rigid tubular outer portion 64 having a circular cross section and a sound insulating liner disposed about the interior thereof. Disposed in conduit 62 at the end thereof removed from reflector plate 44 is a sensing means 70 for receiving the ultrasonic signal and converting it to an electrical signal. A suitable sensing means is a TR-89B/Type 40 signal converter manufactured by MASSA Products Corporation of Hingham, Mass.

Figure 2:
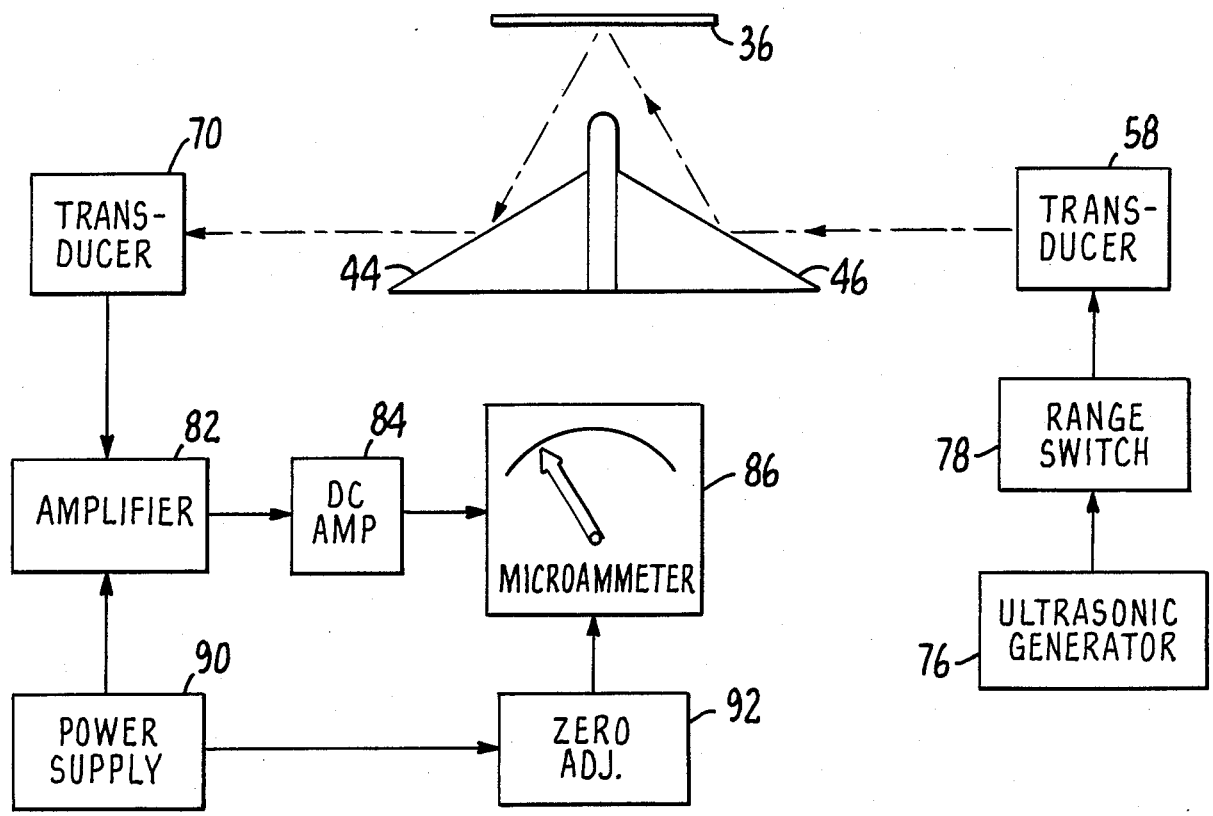
FIG. 2 is a block diagram illustrating the primary components of the apparatus and energy flow between the components during operation of the apparatus.

Referring now to FIG. 2, a block diagram illustrates the primary components of the preferred form of apparatus constructed in accordance with the teachings of the present invention. Arrows between the components show energy flow when the apparatus is in operation. An ultrasonic generator 76 of any suitable type generates a signal which passes through range switch 78 to transducer 58. As previously stated, the transmitter means for transmitting ultrasonic energy 58 is preferably a piezoelectric crystal transducer. One suitable such device is the model TR89 signal transducer manufactured by MASSA Products Corporation.

The ultrasonic generator 76 may be of any suitable type. For example, one means employable for driving or exciting the ultrasonic transducer 58 is the model 420 function generator manufactured by Simpson Company of Elgin, Ill. As may be seen in FIG. 1, the ultrasonic generator 76 is preferably incorporated in housing 10 and secured thereto.

As previously stated, the ultrasonic signal produced by transducer 58 reflects from reflector plate 46 to the paper specimen being tested. The portion of the ultrasonic energy reflected from the sample is then reflected by reflector plate 44 to sensor 70. Sensor 70 receives the ultrasonic signal and converts it to an electrical signal.

The electrical signal produced by sensor 70 is fed to amplifier 82, the output of which is connected to D.C. amplifier 84. The output of D.C. amplifier 84 is fed to microammeter 86 which provides a direct readout of the amplified signal. Obviously a digital readout could be employed if desired. A suitable power supply 90 provides power for the amplifiers and zero adjust potentiometer 92. Amplifiers 82, 84 and power supply 90 may be disposed in housing 10 within a single structural unit 93 as shown in FIG. 1.

Figure 3:
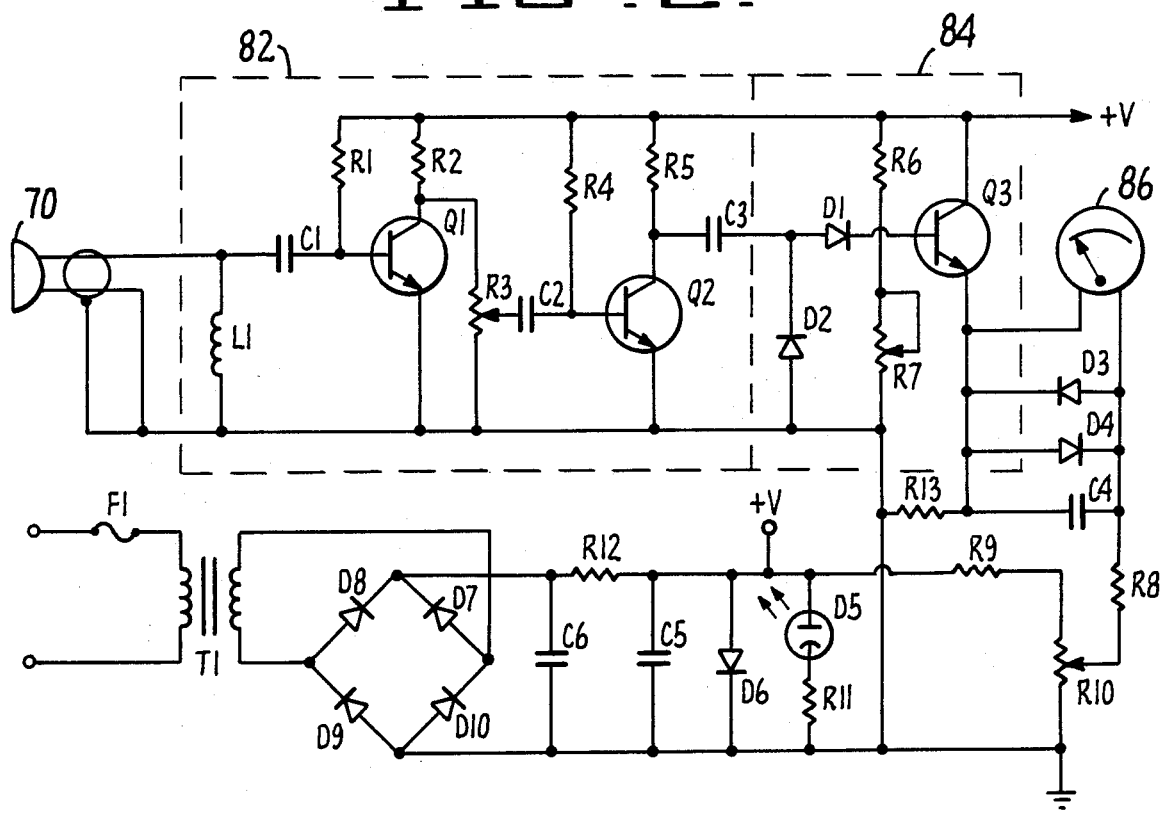
FIG. 3 is a schematic diagram of the amplifier and power supply components of the preferred form of apparatus.

FIG. 3 is a schematic diagram of exemplary amplifier, power supply and related components of the apparatus shown in FIG. 1. The portions of the schematic pertaining to the amplifier 82 and D.C. amplifier 84 have been indicated. The electrical components illustrated in the schematic diagram have the values indicated below.

| Capacitors | | Resistors | |
|---|---|---|---|
| C1, C2, C3 | 0.1 mf | R1 | 4.7 M |
| C4 | 2 mf | R2, R5 | 10K |
| C5 | 250 mf | R3 | 50K |
| C6 | 50 mf | R4 | 5.6 M |
| | | R6 | 1.5 M |
| | | R7 | 100K |
| | | R9 | 6.8K |
| | | R8, R10, R12 | 1K |
| | | R11 | 750 |
| | | R13 | 82K |

| Diodes | |
|---|---|
| D1, D2 | TCG109 |
| D3, D4 | TN4003 |
| D5 | LED |
| D6 | 1N4742 |
| D7 to D10-KBP06 (Bridge Rectifier) | |

| Miscellaneous | |
|---|---|
| F1 | 3AG, 1A Fuse |
| L1 | 10 MH Choke |
| 86 | 50 Microamp Meter |
| Q1, Q2, Q3 | 2N3391 Transistors |
| T1 | 24 V, 200 MA Transformer |
| 70 | Piezoelectric Transducer |

For proper operation of the apparatus, ultrasonic energy should be transmitted at a frequency of at least about 20,000 cycles per second, and preferably in the order of about 40,000 cycles per second.

FIGS. 4 and 5 illustrate another form of the invention particularly adapted to measure the softness of a moving web sample W. The modified device includes a housing 110 mounted on a suitable support such as tripod 112 as by means of a tripod mounting screw 114. Projecting from the housing 110 are flange elements 116, 118. The outer portions of the flange elements define a sampling station in the form of flat and smooth support surfaces which are brought into engagement with the web. The web W is thus maintained in a flat plane as it passes over the housing.

Another difference between the device of FIGS. 4 and 5 as compared with that of FIGS. 1-3 resides in the fact that the ultrasonic signal is not reflected by reflector plates. Rather, the transmitted signal proceeds directly from piezoelectric transducer 120 to the paper. Likewise, the reflected portion of the signal proceeds from the surface of web W directly to sensor 122. Collimation of the energy occurs because the transmitted signal is confined within a generally cylindrical passageway 125 association with transducer 120, said passageway 125 comprising means for directing the signal. A similar passageway 127 leads to the sensor. As with the previously described embodiment, the housing 110 contains suitable sound insulation. Flange elements 116, 118 are preferably connected at their ends by end walls (not shown) to form a closed sound insulated box-like enclosure.

I claim:

1. Paper softness testing apparatus comprising, in combination:
   transmitter means for transmitting ultrasonic energy;
   a station for accomodating the paper to be tested;
   means for directing the transmitted ultrasonic energy to paper located at said station whereby a portion of the transmitted ultrasonic energy is reflected from said paper as a function of the number of bonding sites per unit area of said paper; and
   sensor means for sensing the magnitude of the reflected ultrasonic energy portion;

2. The apparatus of claim 1 wherein said transmitter means comprises an ultrasonic energy signal transducer and wherein said apparatus additionally comprises means for driving said transducer.

3. The apparatus of claim 2 wherein said transducer comprises a piezoelectric crystal.

4. The apparatus of claim 1 wherein the means for directing the transmitted ultrasonic energy to the paper includes a conduit leading from said transmitter means and reflector means for receiving the transmitted ultrasonic energy and reflecting said transmitted ultrasonic energy to said paper.

5. The apparatus of claim 4 wherein said conduit comprises a rigid outer portion defining an interior having a circular cross section and sound insulation disposed about said interior.

6. The apparatus of claim 1 additionally comprising means for directing the reflected energy portion to the sensor means including a conduit leading to said sensor means and reflector means disposed in the path of said reflected ultrasonic energy portion for introducing said reflected ultrasonic energy portion into said conduit.

7. The apparatus of claim 6 wherein said conduit comprises a rigid outer portion defining an interior having a circular cross section and sound insulation disposed about said interior.

8. The apparatus of claim 1 additionally comprising energy absorption means for absorbing any transmitted ultrasonic energy passing through said paper.

9. The apparatus of claim 1 additionally comprising means for directing the reflected energy portion to the sensor means and wherein the means for directing the transmitted ultrasonic energy and the means for directing the reflected ultrasonic energy portion each includes reflector means having reflection surfaces, the reflector means being disposed between the transmitter means and the sensor means.

10. The apparatus of claim 9 wherein said reflector means are positioned on a base and both said reflector surfaces extend toward one another from spaced locations on said base to form a generally triangular configuration.

11. The apparatus of claim 10 wherein the included angles between one reflector surface and the base and the other reflector surface and the base are substantially equal.

12. The apparatus of claim 11 wherein the included angles are each in the order of 30°.

13. The apparatus of claim 5 wherein the transmitter means includes a circular transmitter surface and wherein the diameter of the cross section of said interior is at least equal in size to the diameter of said transmitter surface.

14. Testing apparatus for testing the softness of paper as a function of the number of bonding sites per unit area of said paper comprising, in combination:
    transmitter means for transmitting ultrasonic energy at a frequency of at least about 20,000 cycles per second;
    a station for accomodating paper to be tested for softness;
    means for directing the transmitted ultrasonic energy to paper located at said station whereby a portion of the transmitted ultrasonic energy is reflected from said paper as a function of the number of bonding sites per unit area of said paper; and
    sensor means for sensing the magnitude of the reflected ultrasonic energy portion.

15. A method of testing the softness of paper comprising the steps of:
    transmitting ultrasonic energy;
    directing said transmitted ultrasonic energy in a substantially sound insulated environment toward paper to be tested;
    impacting said transmitted ultrasonic energy on a surface of said paper whereby a portion of the transmitted ultrasonic energy is reflected from said paper as a function of the number of bonding sites per unit area of said paper; and
    sensing the portion of said ultrasonic energy reflected from said paper surface.

16. The method of claim 15 wherein said ultrasonic energy is transmitted at a frequency of at least about 20,000 cycles per second.

17. The method of claim 15 wherein said ultrasonic energy is transmitted at a frequency in the order of about 40,000 cycles per second.

18. The method of claim 15 wherein said transmitted ultrasonic energy is in the form of a collimated beam prior to impacting on said paper surface.

19. The method of claim 18 wherein said collimated beam of ultrasonic energy is formed by passing said transmitted ultrasonic energy through an elongated throughbore of generally uniform cross section.

20. The method of claim 18 additionally comprising the step of changing the direction of said collimated beam prior to impacting said collimated beam on said paper surface by reflecting said collimated beam from a reflecting surface.

21. The method of claim 20 wherein the direction of said collimated beam is changed in the order of about sixty degrees.

22. A method of testing the softness of paper comprising the steps of:
    postioning paper having a flat surface at a predetermined location;
    impacting a collimated beam of ultrasonic energy on said paper surface at an angle of incidence less than ninety degrees;
    reflecting a portion of said collimated beam of ultrasonic energy from said surface as a function of the softness of the paper; and
    sensing the portion of ultrasonic energy reflected from said surface.

* * * * *